Dec. 28, 1965 J. W. PLOETZ Plant Pat. 2,581
MAPLE TREE
Filed Feb. 7, 1964
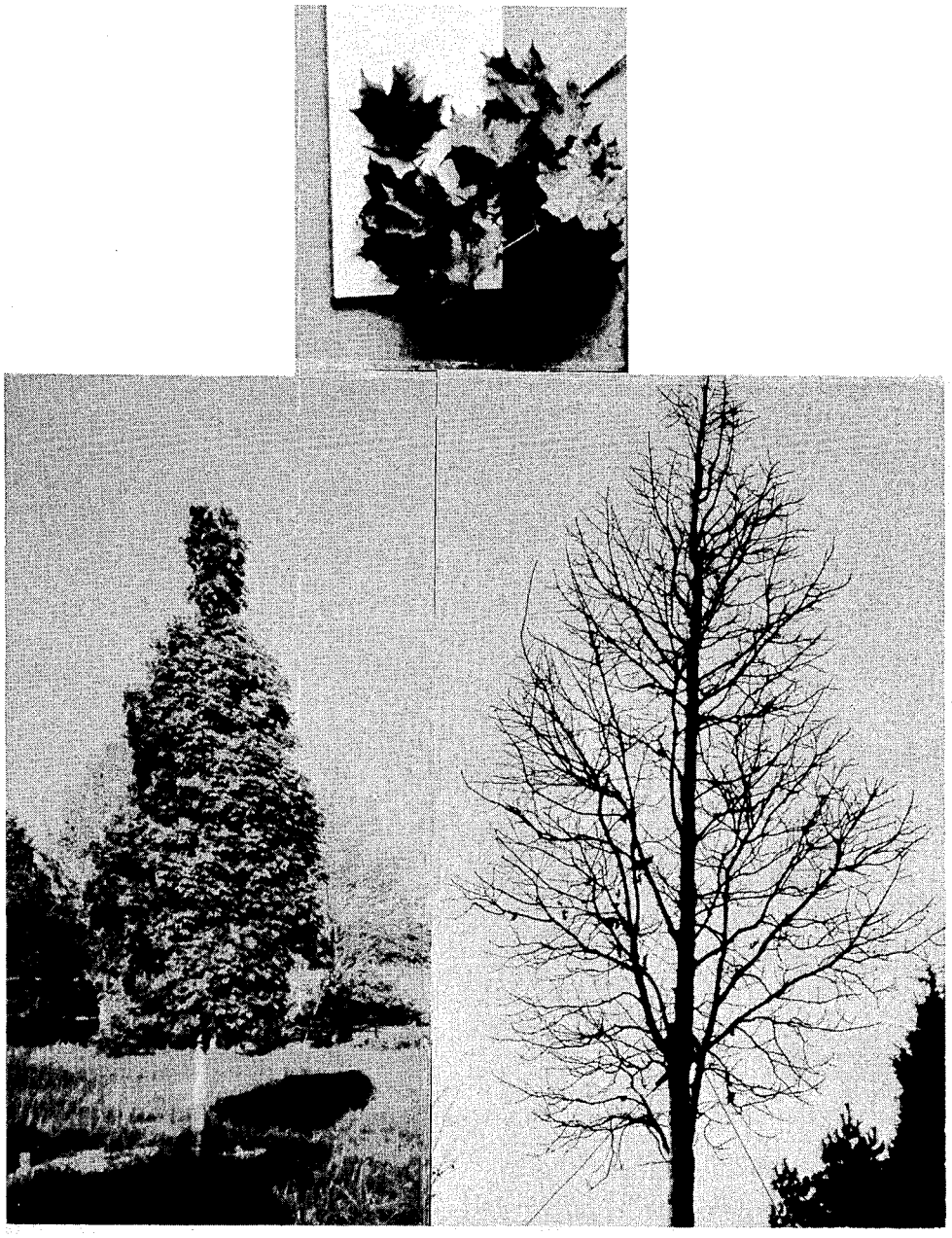
Inventor.
John W. Ploetz
By: Robb & Robb
Attorneys.

United States Patent Office

Plant Pat. 2,581

Patented Dec. 28, 1965

2,581

MAPLE TREE

John W. Ploetz, Monsey, N.Y., assignor to Mary Flagler Cary, New York, N.Y.

Filed Feb. 7, 1964, Ser. No. 343,427
1 Claim. (Cl. Plt.—51)

The present invention relates to a new and distinct variety of maple tree which was discovered by me as an apparent seed mutation of unknown parentage, but presumably originating from an unnamed and unpatented variety of sugar maple *Acer saccharum*.

At the time of my discovery aforementioned, I was engaged in trimming and moving trees on the estate of my assignee, known as "Cannoo Hills," near Millbrook, New York. In the course of this work, I noticed an unusual tree growing among native sugar maples in one of the fields on the estate. My attention was primarily attracted to this tree by its unusually densely branched and perfectly shaped habits of growth, and the further fact that the leaves were much smaller than those of the adjacent sugar maples. Accordingly, steps were promptly taken to move this unusual tree to a separate field where it could be better preserved and kept under close observation. Continued observations of the original tree and all progeny derived thereform as the result of propagation by both cuttings and grafting, as performed under my direction, fully confirmed the unusual characteristics referred to above, along with other differences, and convinced me that this new mutation definitely is a new variety which is distinguished from all other varieties of sugar maple of which I am aware, as evidenced by the following unique combination of features which are outstanding therein:

(1) Extremely compact, dwarfish and slow habits of growth, with the rate of growth from about ⅓ to ½ the rate of regular sugar maples, regardless of heavy fertilization and/or watering;
(2) A dense branching habit and perfect shape without trimming or pruning, but the tree being more slender than the regular sugar maples;
(3) Small leaves which are retained longer than those of regular sugar maples by reason of the fact that the innermost small branchlets remain alive and hold their leaves longer;
(4) A deep rooting habit; and
(5) Comparative freedom from the usual insect damage and diseases to which sugar maples are normally subject, as determined by comparison with other varieties grown under comparable cultural conditions near Millbrook, New York.

The accompanying drawing shows a typical specimen tree of the new variety, as depicted in black and white to illustrate its general form and habit of growth, with additional views showing the tree without foliage and typical specimen leaves depicted on a larger scale than those in the view which shows the tree in foliage.

The following is a detailed description of my new variety, with color terminology in accordance with Koster's Color Guide:

Parentage: Seed mutation of unknown parentage.
Locality where grown and observed: Millbrook, New York.
Tree: Small size; upright; dense; hardy.
*Trunk.*—Smooth; similar to regular sugar maple.
*Branches.*—Stocky (more stocky than branches and twigs of regular sugar maple); smooth, but not conspicuously different from regular sugar maple as regards bark smoothness. Color: Same as regular sugar maple.
*Rate of growth.*—Slow; during the past five years, about 6.7 inches, as compared with 17.8 inches which is the normal rate of growth of regular sugar maples in the same area under comparable conditions.
*Lenticels.*—Approximately four times as numerous as in the regular sugar maple per unit length of internode; roundish in shape as compared with the more elongate form in the regular sugar maples.
Foliage:
*Leaves.*—Quantity: abundant. Size: approximately ½ size of regular sugar maple leaves; length (blade)—2.8 inches, as compared with 4.1 inches for regular sugar maple leaves; width—3.5 inches, as compared with 5 inches for regular sugar maple leaves. Shape: 3 lobed; same as shape of regular sugar maple leaves. Thickness: medium. Color: upper side—near Taxus Green, Plate 81; under side—near Artichoke Green, Plate 72. Petiole: variable length, depending on leaf position as in regular sugar maple leaves.

*General observations*

Although the general appearance of my new variety of maple tree is narrowly upright, its skeletal framework reveals no lateral branches that grow parallel-upright in relation to the main axis. Most of its branches grow outward and upward as is typical of most normal species, contrary to the fastigiate forms such as "Temple's Upright" (unpatented), "Newton Sentry" (unpatented), and others. The leaf size of my new variety is smaller than either of the aforementioned named varieties and less than half the size of the leaves of "Temple's Upright," while the under side of the leaves of my new variety is densely silky, hairy on the main veins and sparsely hairy on the veinlets, contrary to the completely glabrous main veins and only tufts of hair in the axils of the larger veins of the leaves of "Newton Sentry," and in contrast with the fine hairs at the sides of the veins and veinlets, with the veinlets more hairy than in "Newton Sentry," in the case of leaves of "Temple's Upright."

The lateral branchlets of regular sugar maples, including the variety known as *Acer saccharum conicum* (unpatented), grow in lengths approximately 2½ times as rapidly as those of my new variety, and neither I, nor recognized experts, have found or have knowledge of any fastigiate variety which possesses the unusually slow growth characteristic of my new variety and which particularly distinguishes my new variety from "Temple's Upright" and "Newton Sentry."

I claim:

A new and distinct variety of maple tree, substantially as herein shown and described, characterized particularly as to novelty by the unique combination of extremely compact, dwarfish and slow habits of growth, a dense branching habit and perfect shape which requires little or no trimming or pruning, small leaves, a deep rooting habit, and good resistance to insects and common diseases to which regular sugar maple varieties are normally subject.

No references cited.

ABRAHAM G. STONE, *Primary Examiner.*
T. GRAHAM CRAVER, *Examiner.*